(12) United States Patent
Fujiwara

(10) Patent No.: US 7,301,620 B2
(45) Date of Patent: Nov. 27, 2007

(54) INSPECTING APPARATUS, IMAGE PICKUP APPARATUS, AND INSPECTING METHOD

(75) Inventor: Takeshi Fujiwara, Yokohama (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 35 days.

(21) Appl. No.: 11/392,656

(22) Filed: Mar. 30, 2006

(65) Prior Publication Data
US 2006/0221332 A1    Oct. 5, 2006

(30) Foreign Application Priority Data
Mar. 31, 2005   (JP) .............................. 2005-100329

(51) Int. Cl.
*G01N 21/00* (2006.01)
(52) U.S. Cl. ................. 356/237.2; 356/237.4
(58) Field of Classification Search .................. None
See application file for complete search history.

(56) References Cited

U.S. PATENT DOCUMENTS 6,831,998 B1 *  12/2004  Koshishiba et al. ........ 382/147
7,032,208 B2 *   4/2006  Yamashita ................... 716/19
2002/0001759 A1 *  1/2002  Ohashi et al. ................. 430/5
2004/0263829 A1 * 12/2004  Ikeda ....................... 356/237.1

FOREIGN PATENT DOCUMENTS

JP          11-72905        3/1999
JP        2003-121984       4/2003

* cited by examiner

*Primary Examiner*—Michael P. Stafira
(74) *Attorney, Agent, or Firm*—Oblon, Spivak, McClelland, Maier & Neustadt, P.C.

(57) ABSTRACT

An inspecting apparatus includes an illuminating optical system which irradiates irradiation light onto an object to be inspected, an object placing stage which moves the object along a first direction, an accumulative sensor which converts a transmitted image of the object into an electric signal, a sensor drive unit which moves the accumulative sensor in the irradiation direction and a second direction crossing the first direction, a moving amount detecting unit which detects a moving amount of the object placing stage in the second direction, a control unit which controls a drive amount of the sensor drive unit in the second direction on the basis of the moving amount in the second direction detected by the moving amount detecting unit, and a data comparing unit which compares the transmitted image data of the object with a reference data to detect a defect of the object.

9 Claims, 4 Drawing Sheets

INSPECTING APPARATUS, IMAGE PICKUP APPARATUS, AND INSPECTING METHOD

CROSS-REFERENCE TO RELATED APPLICATIONS

This application is based upon and claims the benefit of priority from prior Japanese Patent Application No. 2005-100329, filed Mar. 31, 2005, the entire contents of which are incorporated herein by reference.

BACKGROUND OF THE INVENTION

1. Field of the Invention

The present invention relates to an inspecting apparatus and an image pickup apparatus which inspect a pattern or the like of a photomask or a wafer used in manufacturing a semiconductor device.

2. Description of the Related Art

As an inspecting apparatus applied to the steps in manufacturing a semiconductor device, a photomask inspection apparatus which inspects a mask pattern of a photomask is known (for example, see Jpn. Pat. Appln. KOKAI Publication No. 11-72905).

FIG. 6 is a diagram for explaining an example of the configuration of a photomask inspection apparatus 10. The photomask inspection apparatus 10 includes a mask image capturing device 20, a reference data generating device 30, and a data comparing circuit 40.

The mask image capturing device 20 includes a laser beam source 21, an illuminating optical system 22 which uniforms a beam from the laser beam source 21 to irradiate the beam onto a photomask M, a condenser lens 23 which guides a beam from the illuminating optical system 22 to the photomask M, a stage 24 on which the photomask M is placed, a stage drive mechanism 25 which moves the stage 24 in an accumulating direction (direction of an arrow X in FIG. 6) perpendicular to an irradiating direction of the stage 24, an object lens 26 to focus a beam transmitted through the photomask M on a TDI (Time Delay and Integration) sensor 27 (to be described later), and the TDI sensor 27 on which pixels are arranged in the accumulating direction and a pixel direction perpendicular to each other. Image data D1 of the photomask M is output from the TDI sensor 27.

The reference data generating device 30 includes a reference data generating circuit 31 which generates C reference data on the basis of design data of the photomask M to output reference data D2 for the photomask. The data comparing circuit 40 has a function that compares the image data D1 of the photomask M with the reference data D2, outputs comparison data D3 on the basis of the result of the comparison, and detects a defect P.

The photomask inspecting apparatus described above has the following problem. That is, the pattern of the photomask is micropatterned to shorten the wavelength of the laser beam source, and the intensity of the beam input to the sensor becomes low. The TDI sensor is an accumulative line sensor, and a weak beam can be amplified by the number of accumulating layers. For this reason, the photomask inspecting apparatus is suitable for highly accurate photomask inspection.

However, when the moving speed of the stage is not matched with accumulating time, an image is blurred disadvantageously. For this reason, in order to cause the TDI sensor to pick up the image of the photomask, image pickup must be performed such that the stage moving speed is determined in accordance with the accumulating time of the TDI sensor. The stage speed calculated on the basis of the accumulating time is not matched with an actual stage moving speed, a blurred image is obtained. For this reason, the accumulating time of the TDI sensor is varied such that the position of the stage can be monitored, and the TDI sensor picks up the image of the photomask while synchronizing positions. The fluctuation in speed in the accumulating direction of the TDI sensor is improved.

On the other hand, even though the stage moves in the pixel direction perpendicular to the accumulating direction, a blurred image or a distorted image is disadvantageously formed. Even though the accumulating time of the TDI sensor is made variable, the problem cannot be solved.

BRIEF SUMMARY OF THE INVENTION

According to an aspect of the present invention, there is provided an inspecting apparatus, comprises: an illuminating optical system which irradiates irradiation light onto an object to be inspected; an object placing stage which moves the object along a first direction crossing an irradiating direction of the irradiation light; an accumulative sensor which converts a transmitted image or a reflected image of the object into an electric signal; a sensor drive unit which moves the accumulative sensor in the irradiation direction and a second direction crossing the first direction; a moving amount detecting unit which detects a moving amount of the object placing stage in the second direction; a control unit which controls a drive amount of the sensor drive unit in the second direction on the basis of the moving amount in the second direction detected by the moving amount detecting unit; a reference data generating unit which generates reference data of the object; and a data comparing unit which compares the transmitted image data or the reflected image data of the object with the reference data to detect a defect of the object.

In addition, according to another aspect of the invention, there is provided an image pickup apparatus, comprises: an illuminating optical system which irradiates irradiation light onto an object to be inspected; an object placing stage which moves the object along a first direction crossing an irradiating direction of the irradiation light; an accumulative sensor which converts a transmitted image or a reflected image of the object into an electric signal; a sensor drive unit which moves the accumulative sensor in the irradiation direction and a second direction crossing the first direction; a moving amount detecting unit which detects a moving amount of the object placing stage in the second direction; and a control unit which controls a drive amount of the sensor drive unit in the second direction on the basis of the moving amount in the second direction detected by the moving amount detecting unit.

Further, according to another aspect of the invention, there is provided an inspecting method, comprising: irradiating irradiation light onto an object to be inspected; placing the object on an object placing stage and moving the object along a first direction crossing an irradiating direction of the irradiation light; converting a transmitted image or a reflected image of the object into an electric signal in an accumulative sensor; moving the accumulative sensor in the irradiation direction and a second direction crossing the first direction; detecting a moving amount of the object placing stage in the second direction; controlling a moving amount of the accumulative sensor in the second direction on the basis of the detected moving amount in the second direction; generating reference data of the object; and comparing the transmitted image data or the reflected image data of the object with the reference data to detect a defect of the object.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiment of the invention, and together with the general description given above and the detailed description of the preferred embodiment given below, serve to explain the principles of the invention.

DETAILED DESCRIPTION OF THE INVENTION

Figure 1:
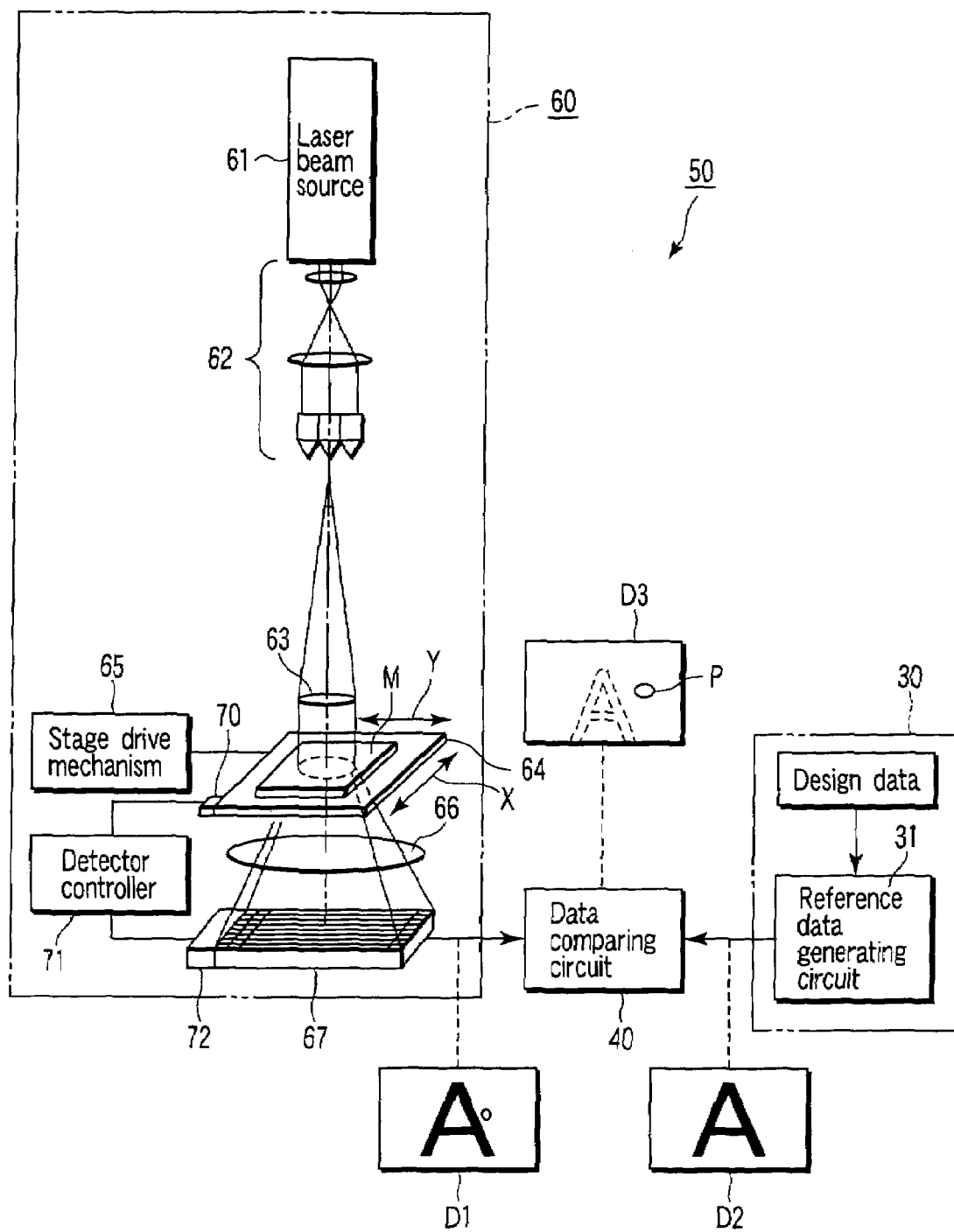
FIG. 1 is a diagram for explaining the configuration of a photomask inspecting apparatus according to an embodiment of the present invention.
Figure 6:
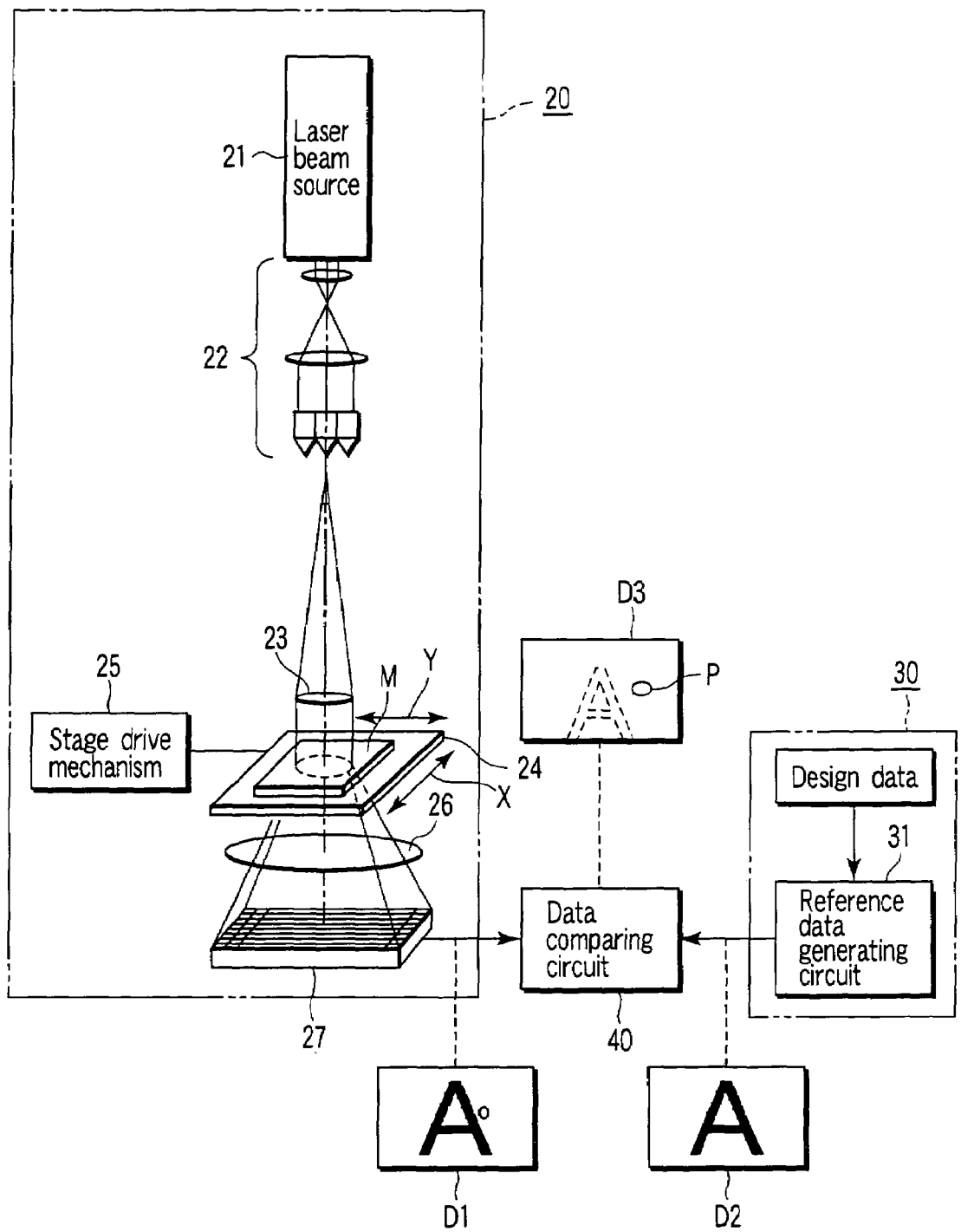
FIG. 6 is a diagram for explaining an example of a conventional photomask inspecting apparatus.

FIG. 1 is a diagram showing the configuration of a photomask inspecting apparatus (inspecting apparatus) 50 according to an embodiment of the present invention. The same reference numerals as those in FIG. 1 denote the same functional parts in FIG. 6. A direction of an arrow X in FIG. 1 denotes an accumulating direction in a TDI (Time Delay and Integration) sensor 67, and a direction of an arrow Y in FIG. 1 denotes a pixel direction perpendicular to the accumulating direction.

The photomask inspecting apparatus 50 includes a mask image capturing device 60, a reference data generating device 30, and a data comparing circuit 40.

The mask image capturing device 60 includes a laser beam source 61, an illuminating optical system 62 which uniforms a beam from the laser beam source 61 to irradiate the beam onto a photomask M, a condenser lens 63 which guides a beam from the illuminating optical system 62 to the photomask M, a stage 64 on which the photomask M is placed, a stage drive mechanism 65 which moves the stage 64 in an accumulating direction (direction of an arrow X in FIG. 1) perpendicular to an irradiating direction of the stage 64, an object lens 66 to focus a beam transmitted through the photomask M on a TDI sensor 67 (to be described later), and the TDI sensor 67 on which pixels are arranged in the accumulating direction and a pixel direction perpendicular to each other.

The TDI sensor 67 is constituted by a photoelectric converter having an arbitrary number of pixels, e.g., about several thousand pixels per line and an arbitrary number of lines, e.g., about several hundred lines. The TDI sensor 67 has a special function that accumulates light intensity output signals from one line in synchronism with a moving speed of the photomask M, i.e., the stage 64 while sequentially adding the light intensity output signals to light intensity output signals from the next line and that, when the intensity signals of all the lines are accumulated, outputs the accumulated signals. In this manner, the TDI sensor 67 outputs image data D1 of the photomask M.

A moving amount detecting sensor 70 is attached to the stage 64. The moving amount detecting sensor 70 detects a moving amount of the stage 64 in the direction of an arrow Y. An output from the moving amount detecting sensor 70 is input to a detector controller 71. The moving amount detecting sensor 70 is constituted by an acceleration sensor, a laser interferometer, or the like.

The detector controller 71 has a feedback control function that calculates a drive amount to the TDI sensor stage 72 (to be described later) on the basis of the moving amount of the stage 64 to output a drive signal to perform correction (to be described later).

The TDI sensor stage 72 has a function that reciprocates the TDI sensor 67 along the direction of the arrow Y in FIG. 1 and is driven on the basis of the drive signal from the detector controller 71.

The reference data generating device 30 includes a reference data generating circuit 31 which generates reference data on the basis of design data of the photomask M and outputs reference data D2 for the photomask. The data comparing circuit 40 has a function that compares the image data D1 of the photomask M with the reference data D2, outputs comparison data D3 on the basis of the result of the comparison, and detects a defect P.

In the photomask inspecting apparatus 50 having the above configuration, defect inspection is performed to the photomask M as follows. More specifically, a laser beam irradiated from the laser beam source 61 is uniformed by the illuminating optical system 62 and then irradiated onto the photomask M through the condenser lens 63. The photomask M moves at a predetermined speed by the stage 64 in the direction of the arrow X in FIG. 1.

A beam transmitted through the photomask M is focused on the TDI sensor 67 through the object lens 66. In the TDI sensor 67, on the basis of the incident transmitted beam, the image data D1 is generated and output to the data comparing circuit 40.

The data comparing circuit 40 compares the image data D1 with the reference data D2, outputs comparison data D3 on the basis of the result of the comparison, and detects the defect P.

Figure 2:
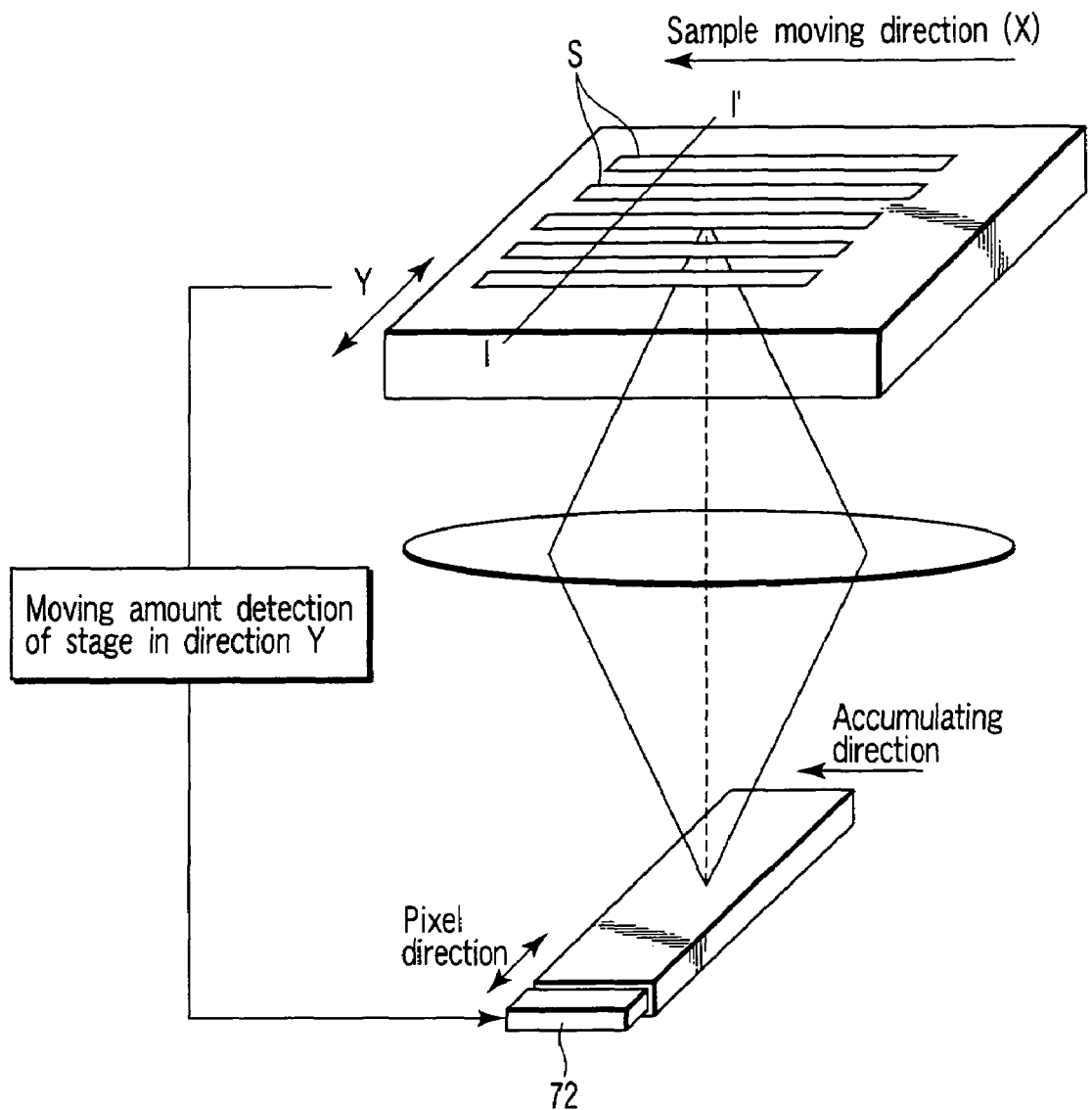
FIG. 2 is a diagram for explaining a control principle of the photomask inspecting apparatus.

Correction by the TDI sensor stage 72 will be described below. A moving amount of the stage 64 in the direction of the arrow Y in FIG. 1 is detected by the moving amount detecting sensor 70. A moving amount within scanning time of 1 line is ignored because the moving amount is accumulated in the TDI sensor 67, and a moving amount for time equal to or longer than the scanning time is measured. A drive amount of the TDI sensor stage 72 is calculated by the detector controller 71 on the basis of the moving amount, and a drive signal is output. The TDI sensor stage 72 drives the TDI sensor 67 on the basis of the drive signal in the direction of an arrow Y in FIG. 1 (FIG. 2).

Figure 3:
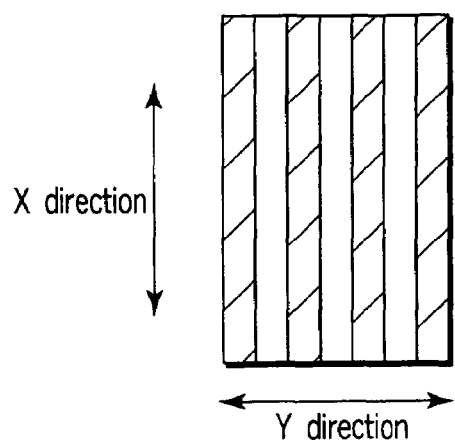
FIG. 3 is a pattern diagram showing an image obtained after control in the photomask inspecting apparatus.

In this manner, if an image at a position indicated by an I-I' line shown in FIG. 2 on, for example, the photomask M is captured, a case in which correction is performed and a case in which correction is not performed are different from each other in the following point. More specifically, when the correction is performed, the moving amount of the stage 64 in the direction Y is corrected and input to the TDI sensor 67. For this reason, as shown in FIG. 3, a pattern S of the photomask M is linearly input, and input with a high contrast (K1).

Figure 4:
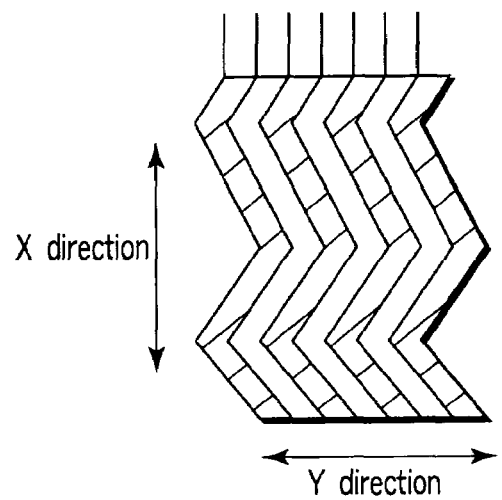
FIG. 4 is a pattern diagram showing an image obtained before control in the photomask inspecting apparatus.
Figure 5:
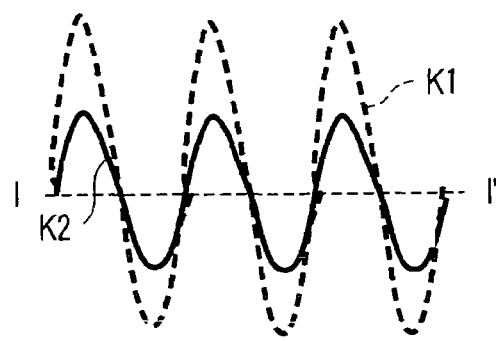
FIG. 5 is a diagram for explaining comparison of contrasts in the photomask inspecting apparatus.

In contrast to this, when the correction is not performed, moving of the stage 64 in the direction Y is directly reflected. Therefore, as shown in FIG. 4, the pattern S of the photomask M is distorted along the moving and input. For this reason, in an accumulated image, a difference between signal intensities as shown in FIG. 5 appears. The image is input as an image of a low contrast (K2). This causes blurring of the image in the image data D1.

As described above, in the photomask inspecting apparatus 50 according to the embodiment, moving of the stage 64 in the pixel direction can be corrected. For this reason, an image is prevented from being blurred, and accurate defect inspection can be performed.

The embodiment described above is a photomask inspecting apparatus. The apparatus may be used as a phtomask-image pickup apparatus that acquires images of photomasks. The present invention is not limited to the use of transmitted images such as photomask images. Rather, it can be applied to images reflected from the opaque objects such as semiconductor wafers. Such a reflected image may be examined to inspect the pattern or the like formed on a semiconductor wafer.

The present invention is not directly limited to the embodiment. The present invention can be realized by modifying constituent elements without departing from the spirit and scope of the invention in the execution phase. Furthermore, various inventions can be formed by appropriate combinations of a plurality of constituent elements disclosed in the embodiment. For example, several constituent elements may be deleted from all the constituent elements described in the embodiment. In addition, constituent elements across different embodiments may be appropriately combined to each other.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An inspecting apparatus comprising:
an illuminating optical system which irradiates irradiation light onto an object to be inspected;
an object placing stage which moves the object along a first direction crossing an irradiating direction of the irradiation light;
an accumulative sensor which converts a transmitted image or a reflected image of the object into an electric signal;
a sensor drive unit which moves the accumulative sensor in the irradiation direction and a second direction crossing the first direction;
a moving amount detecting unit which detects a moving amount of the object placing stage in the second direction;
a control unit which controls a drive amount of the sensor drive unit in the second direction on the basis of the moving amount in the second direction detected by the moving amount detecting unit;
a reference data generating unit which generates reference data of the object; and
a data comparing unit which compares the transmitted image data outputted from the accumulative sensor or the reflected image data of the object outputted from the accumulative sensor with the reference data to detect a defect of the object.

2. The inspecting apparatus according to claim 1, wherein the reference data is generated on the basis of design data of the object.

3. The inspecting apparatus according to claim 1, wherein the reference data is generated on the basis of object image data obtained by performing image pickup operations at different times.

4. An image pickup apparatus comprising:
an illuminating optical system which irradiates irradiation light onto an object to be inspected;
an object placing stage which moves the object along a first direction crossing an irradiating direction of the irradiation light;
an accumulative sensor which converts a transmitted image or a reflected image of the object into an electric signal;
a sensor drive unit which moves the accumulative sensor in the irradiation direction and a second direction crossing the first direction;
a moving amount detecting unit which detects a moving amount of the object placing stage in the second direction; and
a control unit which controls a drive amount of the sensor drive unit in the second direction on the basis of the moving amount in the second direction detected by the moving amount detecting unit.

5. An inspecting method comprising:
irradiating irradiation light onto an object to be inspected;
placing the object on an object placing stage and moving the object along a first direction crossing an irradiating direction of the irradiation light;
converting a transmitted image or a reflected image of the object into an electric signal in an accumulative sensor;
moving the accumulative sensor in the irradiation direction and a second direction crossing the first direction;
detecting a moving amount of the object placing stage in the second direction;
controlling a moving amount of the accumulative sensor in the second direction on the basis of the detected moving amount in the second direction;
generating reference data of the object; and
comparing the transmitted image data outputted from the accumulative sensor or the reflected image data of the object outputted from the accumulative sensor with the reference data to detect a defect of the object.

6. The inspecting method according to claim 5, wherein the reference data is generated on the basis of design data of the object.

7. The inspecting method according to claim 5, wherein the reference data is generated on the basis of object image data obtained by performing image pickup operations at different times.

8. The inspecting method according to claim 5, wherein the object is a photomask substrate.

9. The inspecting method according to claim 5, wherein the object is a semiconductor wafer.

* * * * *